United States Patent
Vetter et al.

(10) Patent No.: US 11,116,535 B2
(45) Date of Patent: Sep. 14, 2021

(54) DEVICES AND METHODS FOR SOFT TISSUE AND ENDOVASCULAR MATERIAL REMOVAL

(71) Applicant: TransMed7, LLC, Portola Valley, CA (US)

(72) Inventors: Eugene H Vetter, Portola Valley, CA (US); James W Vetter, Portola Valley, CA (US)

(73) Assignee: TransMed7 LLC, Portola Valley, CA (US)

(*) Notice: Subject to any disclaimer, the term of this patent is extended or adjusted under 35 U.S.C. 154(b) by 407 days.

(21) Appl. No.: 16/278,069

(22) Filed: Feb. 16, 2019

(65) Prior Publication Data
US 2019/0175205 A1   Jun. 13, 2019

Related U.S. Application Data

(62) Division of application No. 15/062,082, filed on Mar. 5, 2016, now Pat. No. 10,219,821.

(60) Provisional application No. 62/129,604, filed on Mar. 6, 2015.

(51) Int. Cl.
| A61B 17/32 | (2006.01) |
| A61B 10/02 | (2006.01) |
| A61B 17/16 | (2006.01) |
| A61B 17/3207 | (2006.01) |

(52) U.S. Cl.
CPC ...... *A61B 17/32002* (2013.01); *A61B 10/025* (2013.01); *A61B 10/0233* (2013.01); *A61B 10/0266* (2013.01); *A61B 10/0283* (2013.01); *A61B 17/1637* (2013.01); *A61B 17/320758* (2013.01); *A61B 2010/0225* (2013.01); *A61B 2017/320024* (2013.01); *A61B 2017/320032* (2013.01); *A61B 2017/320775* (2013.01)

(58) Field of Classification Search
CPC .............. A61B 10/0233; A61B 10/025; A61B 10/0255; A61B 10/0266; A61B 17/32002; A61B 2010/0225
See application file for complete search history.

(56) References Cited

U.S. PATENT DOCUMENTS

| 3,850,158 | A * | 11/1974 | Elias | A61B 10/025 600/567 |
| 5,350,393 | A * | 9/1994 | Yoon | A61B 10/0233 604/164.12 |
| 8,506,475 | B2 * | 8/2013 | Brannon | A61B 1/313 600/114 |
| 2007/0239109 | A1* | 10/2007 | Dereuil | A61B 17/32002 604/96.01 |
| 2011/0105841 | A1* | 5/2011 | Kutikov | A61B 10/0233 600/104 |
| 2014/0358029 | A1* | 12/2014 | Vetter | A61B 10/0266 600/567 |

* cited by examiner

*Primary Examiner* — Daniel L Cerioni
*Assistant Examiner* — Raymond P Dulman
(74) *Attorney, Agent, or Firm* — Young Law Firm, P.C.

(57) ABSTRACT

A soft tissue biopsy or material collection device may comprise a work element consisting of an outer tube with external sheath and formed from a tapered helical structure over an internal tube structure configured to open and close its distal end to perform penetration, coring, capturing, parting off and transporting multiple material samples in a single or multiple insertion procedure.

11 Claims, 5 Drawing Sheets

DEVICES AND METHODS FOR SOFT TISSUE AND ENDOVASCULAR MATERIAL REMOVAL

BACKGROUND

Embodiments relate to medical devices and methods. More particularly, embodiments relate to devices and methods for soft tissue biopsy, tissue removal and endovascular material removal.

SUMMARY

Embodiments are drawn to medical devices and methods that are used for soft tissue biopsies, solid and semi-solid material removal, de-bulking, and endovascular applications, as described herein. Embodiments may comprise structures and functionality for single insertion, single sample, and single insertion, multiple sample applications and procedures. Embodiments may comprise structures and functionality for soft and hard tissue penetration, coring, capturing, parting off and retrieving or transporting tissue and other materials for pathologic analysis, organ reduction or vascular clearing procedures. Embodiments may be portable, disposable or reusable and may be electrically, mechanically and/or manually powered and operated.

DETAILED DESCRIPTION

Reference will now be made in detail to the construction and operation of embodiments illustrated in the accompanying drawings. The following description is only exemplary of the embodiments described and shown herein. The embodiments, therefore, are not limited to these implementations, but may be realized by other implementations.

A soft tissue biopsy or material removal device as described herein, according to embodiments, may be used to penetrate, core, capture, part off and retrieve tissue or other materials in vivo as part or all of an interventional procedure. The device may be used to perform single insertion-single or multiple sample biopsies of internal organs or structures, such as in the field of breast health, and may also perform de-bulking procedures related to various procedures in the fields of urologic and orthopedic surgery. Further, according to device and method embodiments, a material removal device with a long and flexible work element may be used for endovascular operations and procedures as a result of its ability to core through hard materials and capture them to prevent downstream embolic complications. According to embodiments, a material removal device may be advantageously introduced to an endovascular structure by itself, through the central lumen of a catheter or other endovascular device, or over a guide wire or guide conduit. The distal end of the device may also itself be used within a vascular structure as a barrier for an open ended atherectomy device approaching it from an opposite direction within the vascular structure to part off against, and may also then be opened to aspirate embolic material downstream, according to methods.

Figure 1:
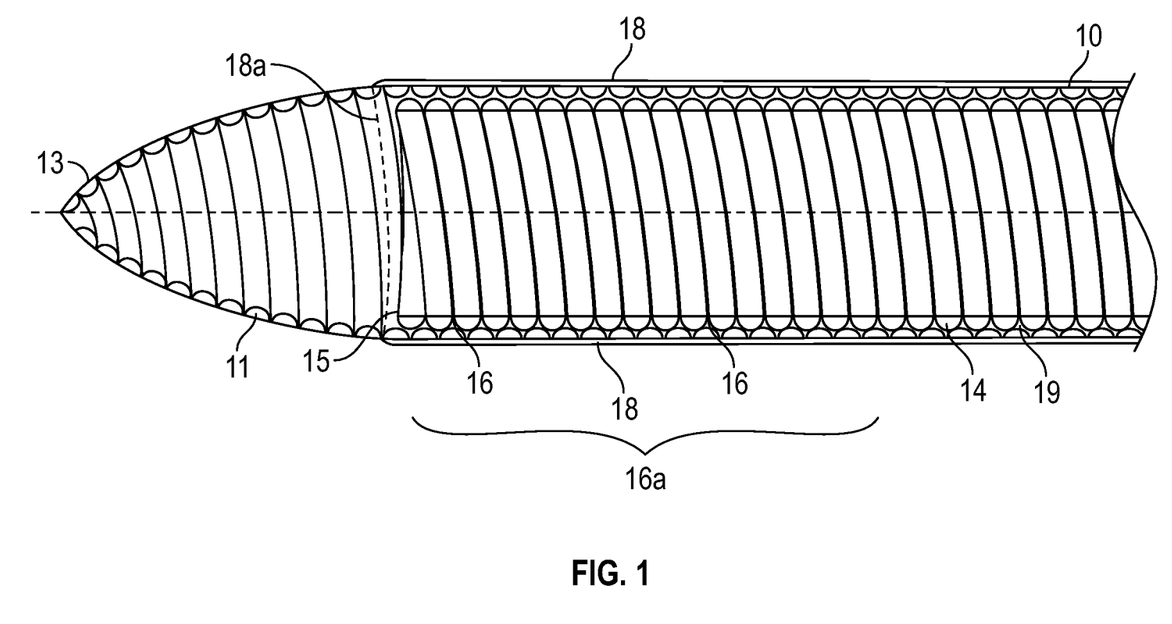
FIG. 1 is a top perspective view of a work element of a material removal device according to one embodiment.

Reference will now be made in detail to the construction and operation of embodiments illustrated in the accompanying drawings. FIG. 1 shows a top down perspective view of a work element 13 (distal end) of a material removal device 10, sliced longitudinally and therefore looking at the inner lumen of one half of the resulting structure, concave to the illustration. Illustrated elements in this figure include a helical outer tube element 11, an inner tube element 14, an internal tube cutting and coring sharpened distal edge 15, internal tube element fusion points 16 in its most distal region 16a, a guide wire 17, an outer sheath 18 and its most distal end 18a, unfused spaces 19 and work element 13 penetration tip 20. According to embodiments, an outer helical tube (also referred to herein simply as "outer tube" or "outer tube element") 11 may be configured as a closely wound helix, which may be laser cut and formed from a single hypo-tube or may be a tightly wound tapered spring, tapering at one end (its distal end 20 or the distal end of the whole work element 13) to a point, and may be completely closed at its point. According to embodiments, a proximal portion of an outer tube element 11 may continue as a helix or may be a tubular structure with various flush ports cut into its structure (not shown).

As shown in this illustration and according to one embodiment, the outer tube element 11 may be formed of a round helical winding of, for instance, stainless steel. An outer tube element 11 may have a smooth external surface as a result of outside grinding, or it may be wound using wire of any cross-section shape, for instance smooth outer or sharpened outer, in order to optimally suit its intended functionality, interaction with soft tissue targets as well as its interaction with other elements of the instrument. The most distal winding of an outer tube element may be shaped and constructed of the same or different cross-section wire for example, to maximize optimized form retention to provide a consistently streamlined shape and to be sharp at its tip 20 to facilitate tissue penetration, for example, by itself or over a guide wire or guide conduit 17, according to embodiments.

An inner tube element 14 of a work element 13 may, according to embodiments, be similarly constructed of a tightly wound helical structure, and may have a sharpened beveled leading edge 15 for coring, as shown in this figure. Such a sharpened leading edge 15 may have different configurations, such as a sine wave, castellations, crenelations, or single or multiple scoopula extensions, and may be sharpened by any of a variety of methods, according to embodiments. An inner tube element thus constructed may be fused, as shown by 16 in this figure, on a certain number of distal windings, as shown by the region 16a, by a process such as laser welding, sheathing, or other configuration. Such an embodiment may be advantageously flexible over its various and entire work element 13 segments for use in endovascular interventions, for example. An inner tube 14 may also have a more proximal region, extending to the handle 12 (shown in FIG. 3) of a device 10, and such proximal region may have unfused interstitial spaces 19 to permit increased flexibility as well as the flow of flush liquids to the lumen of the inner tube element 14, according to embodiments. As shown in this figure, an inner tube element 14 may be bored smooth on its luminal side to aid in transport of collected materials to the handle 12 or other collection structure of a device 10.

According to embodiments either or both of inner tube element 14 as well as outer tube element 11 may be coated with PTFE and PET or other suitable flexible material to impart desired surface characteristics for best transport and to provide structural integrity between un-fused coils or even more open coils, particularly over lengthy segments while not adding substantially to wall thicknesses. These coatings themselves can be given fenestrations through which fluids, vacuum and small particulates may be transmitted. As shown, with an externally ground surface on the outer tube element 11 and an internally ground surface on the internal tube 14, a very low profile work element 13 for coring may be achieved, according to one embodiment. According to embodiments, and as illustrated in this figure, it may be envisioned that if a differential rotational force is applied to the inner tube element 14 and to the outer tube element 11, in this case holding the internal tube stationary while applying a clockwise rotational force (assuming looking from the tip 20 proximally to the right side of the illustration) to the outer tube element 11, that the helical windings distal to the outer sheath 18 distal extension 18a will tend to withdraw proximally and ride up over the inner tube element 14 until the distal coring tip of inner tube element is exposed distally. It should be noted that even with a perfectly smooth inner tube element 14 (i.e., no matched windings in relation to outer tube element 11 windings) if a simultaneous proximal force is applied to the outer tube element 11 while under differential rotation to the inner tube element 14, that the tip 20 of the outer tube element 11 will withdraw over the external surface of the inner tube element 14, allowing the coring tip 15 to be exposed.

The work element 13 may be closed by a corresponding opposite action. This closing action may be enhanced by a flexible inner coating that would, in resting state, preferentially assume a closed state as well, further stabilizing the shape of work element 13 while at the same time providing additional closing forces to the windings of work element 13. The inner coating may be made of a material or composite of materials to impart the desired characteristics of low surface friction as well as additional closing tension. As shown, and according to one embodiment, the distal region 16a of the inner tube element 14 is fused to prevent the outer tube element 11 windings or tip penetrating to the lumen of the inner tube element 14 when differential rotation is applied to the two tube elements to open or close the distal tip 20 of work element 13. Though these windings are shown as tightly wound next to one another, it can be assumed that these may have enough space between windings to allow outer tube element 11 windings to nest neatly between those of fused (at an appropriate distance) less closely wound inner element 14 windings. As shown, this embodiment and those described allow for a very short and rigid distal section of a work element 13 while the remainder of the proximal length of the work element may be very flexible, and the opening and closing of the distal tip 20 of the work element 13 may be controlled from the proximal end of a device 10, even with a very lengthy work element 13, which may attain a length of several feet or more, according to embodiments.

Once exposed, the coring tip 15 of the work element 13 may be rotated to core tissue or other materials, at rotation speeds of very small numbers of revolutions per minute up to very high revolutions per minute, according to embodiments. Both inner and outer tube elements 14, 11 may be rotated synchronously to produce a coring function. Once the specimen or material to be collected is cored, the inner tube element may be held stationary or in differential rotation in relation to the outer tube element rotating counterclockwise to assume its original closed configuration to capture and part off materials in preparation for collection and/or transport to the proximal end of device 10. According to embodiments, the proximal mechanism may include rotating both inner tube element 14 and outer tube element 11 together at the same speed and in the same direction once the work element 13 is in the desired position with respect to edges 15a and 18a, and then when the movements of work element 13 as described are desired, simply lagging the rotation of inner tube element 14 with respect to outer tube element 11 and vice versa would result in the desired actions of work element 13. Once the desired positions are reached, both inner tube element 14 and outer tube element 11 would be caused by a proximal control mechanism to resume equal rotation together to maintain the position of work element 13.

According to embodiments outer tube element 11 and inner tube element 14 may continue to be rotated differentially for example lagging with respect to each other, such that upon reaching full part-off position where work element 13 can no longer be any further closed, there could continue to be differential rotation of inner tube element 14 and outer tube element 11 for the purpose of aiding transport of tissues proximally. This continued discordant (differential) rotation of the two elements 14 and 11 may cause inner tube element 14 to alternately skip over and back again, coils of outer tube element 11, which may act to provide repetitive squeezing and releasing of materials to enable fluids and vacuum access to more surface area of materials being transported to facilitate rapid movement of tissues from distal to proximal within the inner lumen of tissue removing device 10. As shown in this figure, the closed configuration of work element 13 may aid in gentle penetration of tissue to a specific site, and the tip 20 may be sharpened to aid in penetration, or relatively blunt to avoid unwanted penetration of a vascular wall, according to embodiments and methods. The tip 20 may represent a final helical winding that may be open at the distal end to closely fit over a guide wire 17 without cutting or damaging the guide wire when the work element 13 is fully closed at its distal end. According to embodiments and by the methods and constructions described, work element 13 may be maintained in its position and shape in penetration mode, while being rotated gently to minimize dynamic friction within the surrounding and adjacent soft tissues, and to aid in gently dividing tissues on the way to the target area to be cored and de-bulked, thus minimizing trauma along its approach pathway.

An outer sheath element 18 may be constructed of various materials, such as stainless steel in rigid work element 13 embodiments, polyimide, PET tubular structures or simple coatings with substances such as PTFE among others to aid in minimizing drag within soft tissues as well as minimizing drag through any guiding catheters used for the purpose of delivering the working end of tissue removal device 10 en site. Materials and structures such as these may also be used in flexible work element 13 embodiments, as examples. As shown in this figure, the space between the outer sheath element 18 and the outer tube element 11 may allow for flush liquids to be delivered to the distal lip seal 18a through the windings of the outer tube element 11 to the lumen of the inner tube element 14 to aid in proximal transport of collected materials after part off and closing of the work element 13.

According to one embodiment, as shown, when the distal tip 20 is in its fully closed configuration, the distal end 18a of the outer sheath element 18 is distal to the coring tip 15, and may thus allow for flush fluids to pass between the helical coils of the outer tube element 11 to the lumen of the inner tube element 14 to aid in transport of collected materials immediately post part off of the material. When the outer tube 11 is proximally withdrawn to the point of exposing the inner tube element 14 coring edge 15, flush liquids will still pass proximally to the inner tube element fused region 16*a* to aid in continuous and simultaneous transport of collected materials during coring of new materials to be collected, according to embodiments and methods. According to embodiments, a vacuum may be applied from the proximal end of device 10 to the central lumen of the inner tube element 14 to aid in transport of collected materials, and a combination of flush delivered to the distal end of the work element 13 via the external sheath 18 and vacuum in the inner lumen of the inner tube element 14 may provide efficient transport of such collected materials.

The outer diameter of the work element 13 may be of any useful dimension, and may range, for example, from approximately 4 gauge to 30 gauge, according to embodiments. The work element 13 may be rigid or flexible, according to embodiments, and may be used to sample an internal organ or structure, or to follow a duct or vascular structure. The overall length of the work element may range from very small dimensions to several feet, depending on the intended use of the device and according to embodiments. It is to be understood, however, that the foregoing dimensions and any dimensions referred to herein are exemplary in nature only. Those of skill in this art will recognize that other dimensions and/or configurations may be implemented, depending upon the application, and that the elements of the device could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting.

Figure 2A:
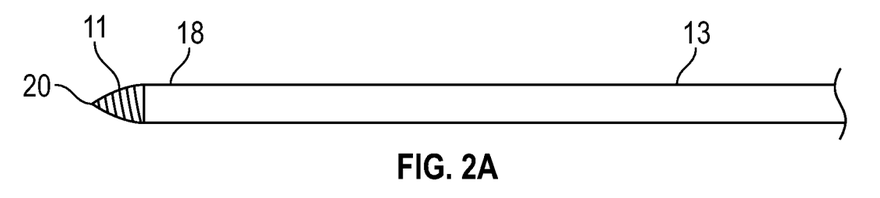
FIGS. 2A, 2B and 2C are perspective views of a work element of a material removal device, according to one embodiment.
Figure 2B:
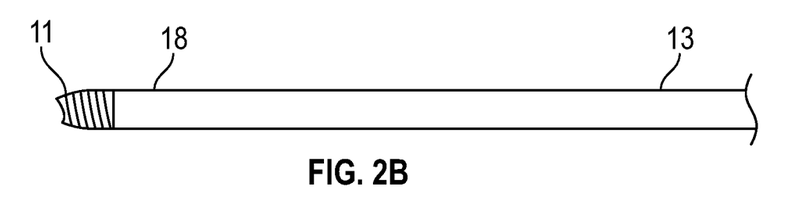
Figure 2C:
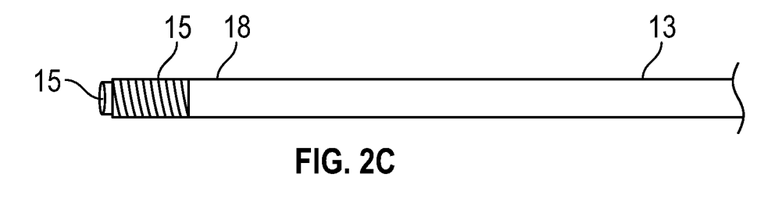

FIGS. 2A, 2B and 2C represent work elements 13 in various stages of opening the outer tube helical element 11 with its outer sheath 18 over the inner tube element 14, not shown in this view, to expose its coring tip 15, according to one embodiment. FIG. 2A shows the work element 13 in its closed, or penetration/part off configuration. FIG. 2B shows the tip 20 of the work element 13 in its partially opened or closed configuration, representing either opening to expose the cutting edge 15 of the inner tube element 14 or to part off a material that has been cored by the cutting edge 15. FIG. 2C illustrates the work element 13 in its fully open, coring configuration.

Figure 3:
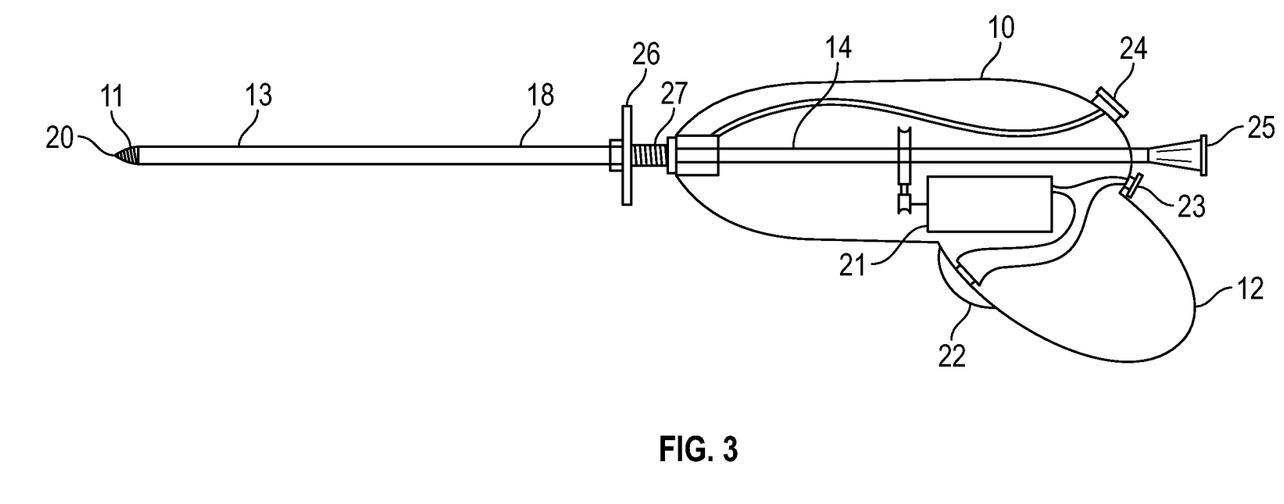
FIG. 3 is a side view of a material removal device, according to one embodiment.

FIG. 3 shows a side, transparent view of a device 10, with work element 13 and various other elements, according to one embodiment. In this view, the handle 12, the work element 13, an internal motor 21 with its pulleys and belt for rotation of the work element 13, a switch 22, an external power plug 23, a flush port 24 to deliver liquids to the distal end of work element 13 via external sheath 18, a distal tip 20, and an external vacuum port 25 are shown. Also shown in a manual control wheel 26 with threaded control portion 27 to differentially rotate the outer tube element 11 in relation to the inner tube element 14 to open and close the distal end of the work element 13. According to one embodiment, actuation of switch 22 rotates the inner and outer tube elements simultaneously for coring, and either manually turning the control wheel 26 while the tubes are stopped or holding it while the tubes are rotating imparts either a distally or proximally directed force on the outer tube element 11 while simultaneously inducing differential rotation between the inner and outer tube elements to open or close the work element 13, depending on the direction of rotation of the work element 13. It may be assumed from this description and illustration that resisting control wheel 26 with any mechanism including a simple friction brake will cause the desired differential rotation of inner tube element 14 with respect to outer tube element 11, which would translate the forces to cause desired movements of work element 13 to fulfill its intended functions including penetration, coring to part-off and complete part-off for example. This type of drag may be of a variable amount sufficient to bring about the desired tension for part-off for example and may be continued beyond part-off to aid tissue transport as outlined in the detail describing FIG. 1. Many different embodiments and configurations of powered and manual operation of such a device 10 may be envisioned, and are considered to be within the scope of this specification and invention.

Figure 4:
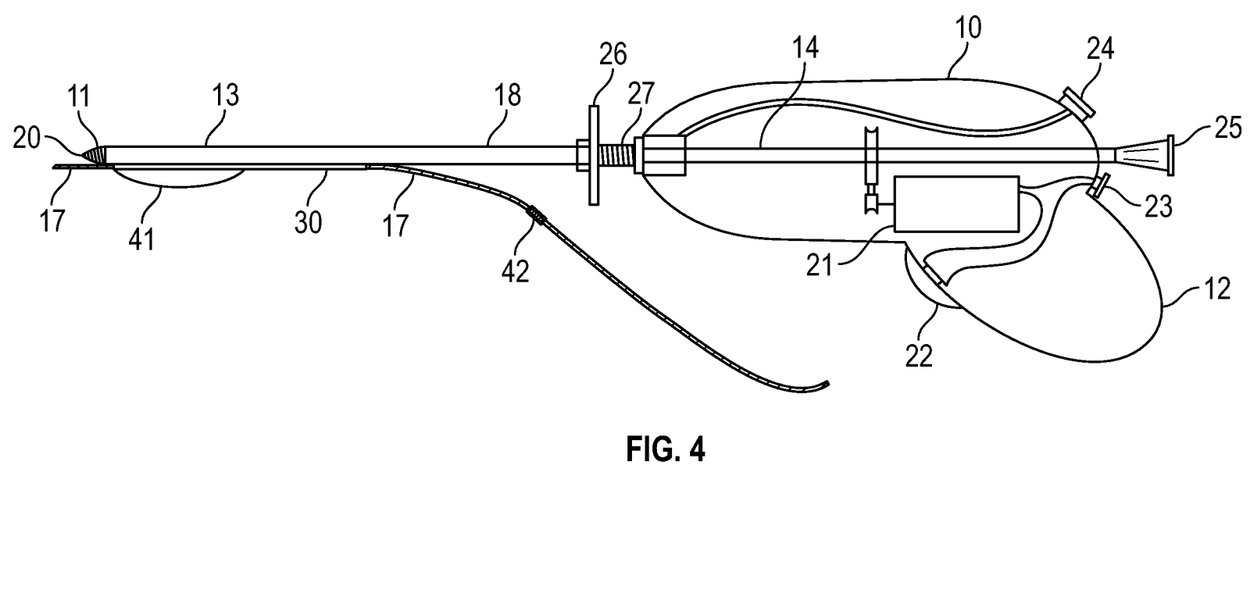
FIG. 4 is a side view of a material removal device, according to one embodiment.

FIG. 4 shows a side, transparent view of a device 10, with work element 13 and various other elements, according to one embodiment. This illustration is similar to FIG. 3 and includes additional detail as well as guide-wire delivering conduit 30, which is shown in a monorail configuration in that the conduit does not proceed full-length through the proximal portions of device 10 for easy exchange of a guide-wire 17 for other instruments such as imaging catheters and wires, guiding elements that may have different characteristics compared to standard guide-wires such as hydrophilic coatings and constructions. This illustration also shows a side-supporting expandable element 41 for use in directing tip 20 to preferentially core in a biased direction opposite expandable element 41 for example. In this embodiment as illustrated, an alternative pathway for guiding elements is shown.

Figure 5:
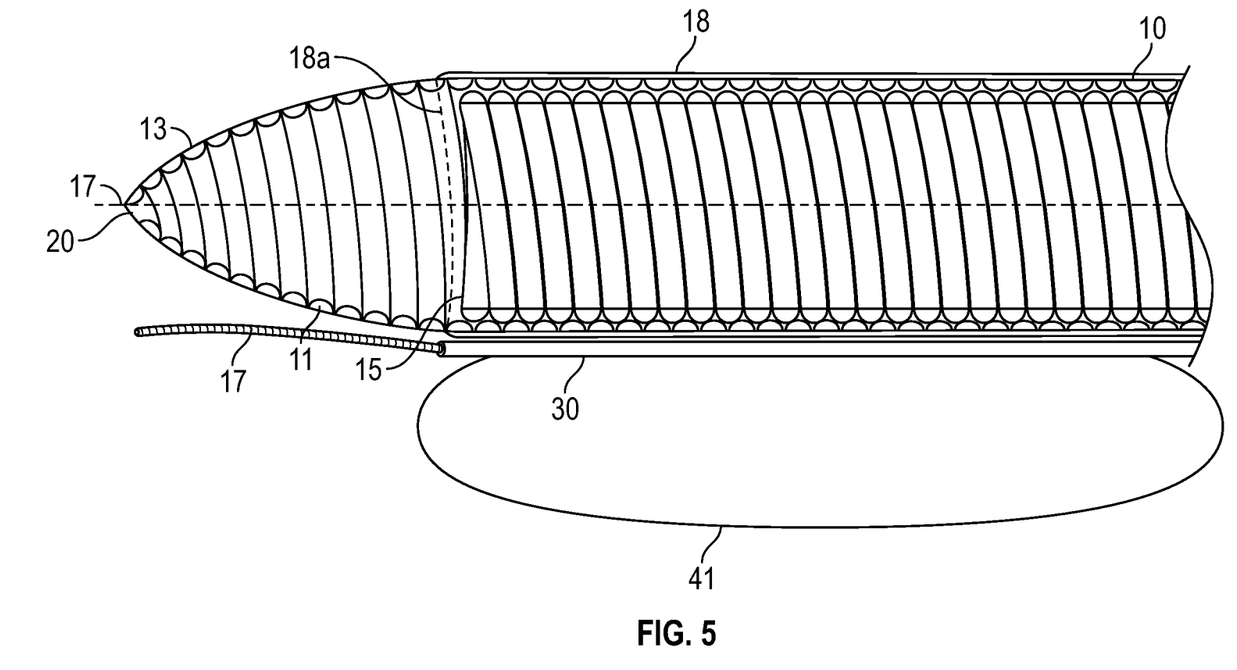
FIG. 5 is a side view of a material removal device, according to one embodiment.

FIG. 5 shows a side view of a work element 13 (distal end) that is similar to the illustration in FIG. 1 of a material removal device 10, sliced longitudinally and therefore looking at the inner lumen of one half of the resulting structure, concave to the illustration, as well as showing additional details from the side view perspective that are not cut away including a side-supporting expandable element 41, along with a guide-element conduit 30 for delivery of guiding wires, guiding imaging elements and agent delivery conduits such as local anesthetic agents, coagulation-promoting agents among others. In this view a guiding wire is shown extending distally through conduit 30, while side-supporting element 41 is shown as an inflated balloon for urging coring via work element 13 in a direction opposite of side-supporting balloon (in this case) 41.

The entire device may be configured to be disposable or may be configured to be reusable in whole or in part. Embodiments of the present device may be electrically powered by one or more batteries and/or external power sources through a simple electrical coupling to connect to an external power supply conveniently placed, for example, in the handle or proximal end of the present biopsy device. The entire device may also be internally or externally manually powered, mechanically powered or be powered by means such as compressed air, gas or pressurized fluid. Powering the device entirely mechanically may be advantageous in areas in which the electric grid is absent, unavailable, or unreliable.

One embodiment is a method of carrying out a soft tissue excision by cutting, parting off and transporting multiple tissue samples via a single access point.

Another embodiment is a method of carrying out a procedure wherein the distal end of the device may also itself be used within a vascular structure as a barrier for an open ended atherectomy device approaching it from an opposite direction within the vascular structure to part off against, and may also then be opened to aspirate embolic material downstream, according to methods.

It is to be understood that the above descriptions are but exemplary methodologies and that one or more of the steps described above may be omitted, while other steps may be added thereto to any of these embodiments, depending on the target site within the body. Other operator method embodiments and device embodiments are supported as well. The order of some of the steps may additionally be changed, according to the desired procedure.

The present device may be formed of or comprise one or more biocompatible materials such as, for example, stainless steel or other biocompatible alloys, and may be made of, comprise or be coated with polymers, such as polyimide, and/or biopolymer materials as needed to optimize function (s). Some of the components may be purposely surface-treated differentially with respect to adjacent components, as detailed. The various gears or pulleys may be made of any suitable, commercially available materials such as nylons, polymers such as moldable plastics, and others. If used, the motor powering the various powered functions of the present biopsy device may be a commercially available electric DC motor. The handle of the present device may likewise be made of or comprise inexpensive, injection-molded plastic or other suitable rigid, easily hand held strong and light-weight material. The handle may be configured in such a way as to make it easily adaptable to one of any number of existing guiding platforms, such as stereotactic table stages. The materials used in the present biopsy device may also be carefully selected from a ferro-magnetic standpoint, such that the present biopsy device maintains compatibility with MRI equipment.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, for example, mechanical linkages or compressed air motors, may be used.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method, comprising:
   providing a device comprising an internal tube element, sharpened at a distal edge thereof, configured to cut and core tissue; and a wound helical coil outer tube element, disposed over the internal tube element, and comprising a distal portion that extends distally beyond the internal tube element in a tapered configuration, such that constituent helical coils thereof define progressively smaller diameters as a distance from the sharpened distal edge of the internal tube element increases;
   inserting at least the distal portion of the wound helical coil outer tube, in the tapered configuration, into tissue;
   retracting the distal tapered portion of the wound helical coil outer tube element, by differentially rotating the wound helical coil outer tube element relative to the internal tube element, to expose the sharpened distal edge of the internal tube element to tissue;
   cutting and coring the tissue;
   parting off the cut and cored tissue by returning the distal tapered portion of the wound helical coil outer tube element to the tapered configuration and enclosing the distal edge of the internal tube, by again differentially rotating the wound helical coil outer tube element relative to the internal tube element.

2. The method of claim 1, wherein the providing is carried out with the device further comprising an outer sheath that is disposed at least partially over the wound helical coil outer tube element.

3. The method of claim 1, wherein the providing is carried out with the wound helical coil outer tube element being formed from a single tube that is laser-cut to form the constituent helical coils thereof.

4. The method of claim 1, wherein the providing is carried out with the wound helical coil outer tube element comprising a tightly wound tapered spring.

5. The method of claim 1, wherein the providing is carried out with at least one of the internal tube element and the wound helical coil outer tube element comprising stainless steel.

6. The method of claim 1, wherein the providing is carried out with the distal portion that extends distally beyond the internal tube element in a tapered configuration being shaped so as to facilitate tissue penetration and parting off cored tissue.

7. The method of claim 1, further comprising:
   fitting a side-supporting expandable element near a distal end of the device; and
   steering the device within tissue by selectively inflating and deflating the side-supporting expandable element.

8. The method of claim 1, wherein the providing is carried out with the wound helical coil outer tube element defining a substantially smooth internal lumen and wherein the method further comprises transporting the cut and cored tissue within the substantially smooth internal lumen.

9. The method of claim 8, further comprising applying suction within the substantially smooth internal lumen of the wound helical coil outer tube element.

10. The method of claim 9, wherein the providing is carried out with the internal tube element comprising a wound helical coil.

11. The method of claim 10 wherein, near a distal portion thereof, the wound helical coil of the internal tube element comprises helical coils that are fused together.

\* \* \* \* \*